(12) United States Patent
Maino et al.

(10) Patent No.: US 7,514,232 B2
(45) Date of Patent: Apr. 7, 2009

(54) METHOD FOR DETECTING T CELL RESPONSE TO SPECIFIC ANTIGENS IN WHOLE BLOOD

(75) Inventors: Vernon C. Maino, Los Altos, CA (US); Maria Suni, Los Gatos, CA (US); Louis J. Picker, Plano, TX (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1213 days.

(21) Appl. No.: 08/803,702

(22) Filed: Feb. 21, 1997

(65) Prior Publication Data

US 2001/0006789 A1 Jul. 5, 2001

Related U.S. Application Data

(63) Continuation-in-part of application No. 08/760,447, filed on Dec. 6, 1996, now abandoned.

(51) Int. Cl.
G01N 33/00 (2006.01)
(52) U.S. Cl. ..................................... 435/7.24
(58) Field of Classification Search ............... None
See application file for complete search history.

(56) References Cited

U.S. PATENT DOCUMENTS

| | | | | |
|---|---|---|---|---|
| 5,093,234 | A | * | 3/1992 | Schwartz |
| 5,407,805 | A | * | 4/1995 | Seon |
| 5,445,939 | A | | 8/1995 | Anderson |
| 5,635,363 | A | | 6/1997 | Altman et al. |
| 5,656,446 | A | | 8/1997 | Anderson |
| 5,843,689 | A | | 12/1998 | Anderson |
| 6,143,299 | A | * | 11/2000 | Srivastava |

OTHER PUBLICATIONS

I. Picker et al. 8G: 1408-1419 (1995).*
Lipsky et al. NY Acad Sci 815: 372-383 (1997).*
BD Application Note 1—Detection of Intracellular Cytokines in Activated Lymphocytes, 1996.*
BD Application Note—23-5195-01 Detecting Cytokines in Antigen-Activated Lymphocytes, 2000.*
Elkeels et al. FEMS Microbiol Lett 116:221-224, 1994.*
Robin et al. Eur J Cell Biol 67:227-237, 1995.*
O'Neill—Andersen Clin Diag Lab Immunol. 243-250, 2002.*
Andersson et al.,"Concomitant in vivo production of 19 different cytokines in human tonsils," *Immunology* 83:16-24 (1994).
Cotner et al.,"Simultaneous flow cytometric analysis of human T cell activation antigen antigen expression and DNA content," *J. Exp. Med.* 157:461-472 (1983).
Elson et al.,"Flow cytometric analysis for cytokine production identifies T Helper1, T Helper 2, and T Helper 0 cells within the human DC4*CD27 lymphocyte subpopulation," *J. of Immunology*, pp. 4294-4300 (1995).
McHeyzer-Williams et al.,"Antigen-specific dvelopment of primary and memory T cells in vivo," *Science* 268:106-11 (Apr. 1995).
Becton Dickinson Immunocytometry Systems, "Detection of Intracellular Cytokines in Activated Lymphocytes," *Application Note 1*, 1-12 (1997).
Brett, S.J. et al., "Limiting Dilution Analysis of the Human T Cell Response to Mycobacterial Antigens from BCG Vaccinated Individuals and Leprosy Patients," *Clin. Exp. Immunol.*, 68:510-520 (1987).
Bucy, R.P. et al., "Heterogeneity of Single Cell Cytokine Gene Expression in Clonal T Cell Populations," *J. Exp. Med.*, 180:1251-1262 (1994).
Clouse, K.A. et al., "Enumeration of Viral Antigen-Reactive Helper T Lymphocytes in Human Peripheral Blood by Limiting Dilution for Analysis of Viral Antigen-Reactive T-Cell Pools in Virus-Seropositive and Virus-Seronegative Individuals," *J. Clin. Microbiol.*, 27(10):2316-2323 (1989).
Davis, M.M. et al., "Ligand Recognition by αβ T Cell Receptors," *Annu. Rev. Immunol.*, 16:523-544 (1998).
Del Prete, G.F. et al., "Purified Protein Derivative of *Mycobacterium tuberculosis* and Excretory-Secretory Antigen(s) of *Toxocara canis* Expand In Vitro Human T Cells with Stable and Opposite (Type 1 T Helper or Type 2 T Helper) Profile of Cytokine Production," *J. Clin. Invest.*, 88:346-350 (1991).
Dobrescu, D. et al., "Enhanced HIV-1 Replication in Vβ12 T Cells Due to Human Cytomegalovirus in Monocytes: Evidence for a Putative Herpesvirus Superantigen," *Cell*, 82:753-763 (1995).
Doherty, P.C., "Cell Mediated Immunity in Virus Infections," *Scand J. Immunol.*, 46:528-540 (1997).
ElGhazali, G.E.B. et al., "Number of Interleukin-4- and Interferon-γ-secreting Human T Cells Reactive with Tetanus Toxoid and the Mycobacterial Antigen PPD or Phytohemagglutinin: Distinct Response Profiles Depending on the Type of Antigen Used for Activation," *Eur. J. Immunol.*, 23:2740-2745 (1993).

(Continued)

*Primary Examiner*—G. R Ewoldt
(74) *Attorney, Agent, or Firm*—Douglas A. Petry

(57) ABSTRACT

This invention comprises a novel approach to the assessment of antigen-specific T cells that quantitates and characterizes these cells with unprecedented clarity, and importantly, because it is performed in whole blood, is amenable to routine use in the clinical immunology laboratory. The methodology offers an improved flow cytometric intracellular cytokine assay in whole blood that can simultaneously measure multiple T cell subsets expressing multiple cytokines from a single whole blood culture. Evaluation of whole blood antigen specific cytokine responses has the important advantage of assessing T cell activation in the presence of ALL types of MHC autologous antigen presenting cells present in the native sample. It also has the advantage of enabling a culture system (whole blood) which can reflect effects of systemic environments (i.e. drug augmentation or suppression) on T cell responses to specific stimuli including antigen, by either culturing in the presence of such drug or analyzing the blood of a human or animal receiving such drug.

41 Claims, 3 Drawing Sheets

OTHER PUBLICATIONS

Germain, R.N., "The Biochemistry and Cell Biology of Antigen Processing and Presentation," *Annu. Rev. Immunol.*, 11:403-450 (1993).

Jung, T. et al., "Detection of Intracellular Cytokines by Flow Cytometry," *J. Immun. Methods*, 159:197-207 (1993).

Kabelitz, D. et al., "Activation-Induced Cell Death (apoptosis) of Mature Peripheral T Lymphocytes," *Immunol. Today*, 14:338-339 (1993).

Komanduri, K.V. et al., "Restoration of Cytomegalovirus-specific CD4* T-lymphocyte Responses After Ganciclovir and Highly Active Antiretroviral Therapy in Individuals Infected with HIV-1," *Nature Medicine*, 4(8):953-956 (1998).

Lanzavecchia, A. et al., "From TCR Engagement to T Cell Activation: A Kinetic View of T Cell Behavior," *Cell*, 96:1-4 (1999).

Lolli, F. et al., "HIV Antigen-Reactive T Cells Detected by Antigen-Induced Interferon γ Secretion," *AIDS Res. and Human Retroviruses*, 10(2):115-120 (1994).

Lolli, F. et al., "T and B Cell Responses to Cytomegalovirus Antigens in Healthy Blood Donors and Bone Marrow Transplant Recipients," *FEMS Immun. and Med. Microbiol.*, 7:55-62 (1993).

Weaver, D. J. Jr. et al., "Macrophage Mediated Processing of an Exogenous Antigenic Fluorescent Probe: Time-dependent Elucidation of the Processing Pathway," *Cell*, 87:95-104 (1996).

Zunino, S.J. et al., "Immunodetection of Histone Epitopes Correlates with Early Stages of Apoptosis in Activated Human Peripheral T Lymphocytes," *Amer. J. Path.*, 149(2):653-663

Mellman, I. et al., "Lonely MHC Molecules Seeking Immunogenic Peptides for Meaningful Relationships," *Current Opinion in Cell Biology*, 7(4):564-572 (1995).

Meyaard, L. et al., "Single-Cell Analysis of Il-4 and IFN-γ Production by T Cells from HIV-Infected Individuals," *J. of Immun.*, 157:2712-2718 (1996).

Openshaw, P. et al., "Heterogeneity of Intracellular Cytokine Synthesis at the Single-Cell Level in Polarized T Helper 1 and T Helper 2 Populations," *J. Exp. Med.*, 182:1357-1367 (1995).

Picker, L.J. et al., "Direct Demonstration of Cytokine Synthesis Heterogeneity Among Human Memory/Effector T Cells by Flow Cytometry," *Blood*, 86(4):1408-1419 (1995).

Prussin, C. et al., "Detection of Intracytoplasmic Cytokine Using Flow Cytometry and Directly Conjugated Anti-cytokine Antibodies," *J. Immun. Methods*, 188:117-128 (1995).

Russell, J.H., "Activation-induced Death of Mature T Cells in the Regulation of Immune Responses," *Current Opinion in Immunology*, 7:382-388 (1995).

Salmon, M. et al., "Production of Lymphokine mRNA by $CD45R^+_{plus+\ +}$ and $CD45R^{+\ plus+\ +}$ Helper T Cells from Human Peripheral Blood and by Human CD4* T Cells Clones," *J. Immunol.*, 143(3):907-912 (1989).

Sornasse, T. et al., "Differentiation and Stability of T Helper 1 and 2 Cells Derived from Naive Human Neonatal $CD4^{+\ plus+\ +}$ T Cells, Analyzed at the Single-cell Level," *J. Exp. Med.*, 184:473-483 (1996).

Suni, M.A. et al., "Detection of Antigen-Specific T Cell Cytokine Expression in Whole Blood by Flow Cytometry," *J. Immunol. Meth.*, 212:89-98 (1998).

Surcel, H.-M. et al., "Th1/Th2 Profiles in Tuberculosis, Based on the Proliferation and Cytokine Response of Blood Lymphocytes to Mycobacterial Antigens," *Immunology*, 81:171-176 (1994).

Waldrop, S.L. et al., "Determination of Antigen-specific Memory/Effector $CD4^{+\ plus+\ +}$ T Cell Frequencies by Flow Cytometry," *J. Clin. Invest.*, 99(7):1739-1750 (1997).

Waldrop, S.L. et al., "Normal Human $CD4^{+\ plus+\ +}$ Memory T Cells Display Broad Heterogeneity in Their Activation Threshold for Cytokine Synthesis," *J. Immun.*, 161:5284-5295 (1998).

* cited by examiner

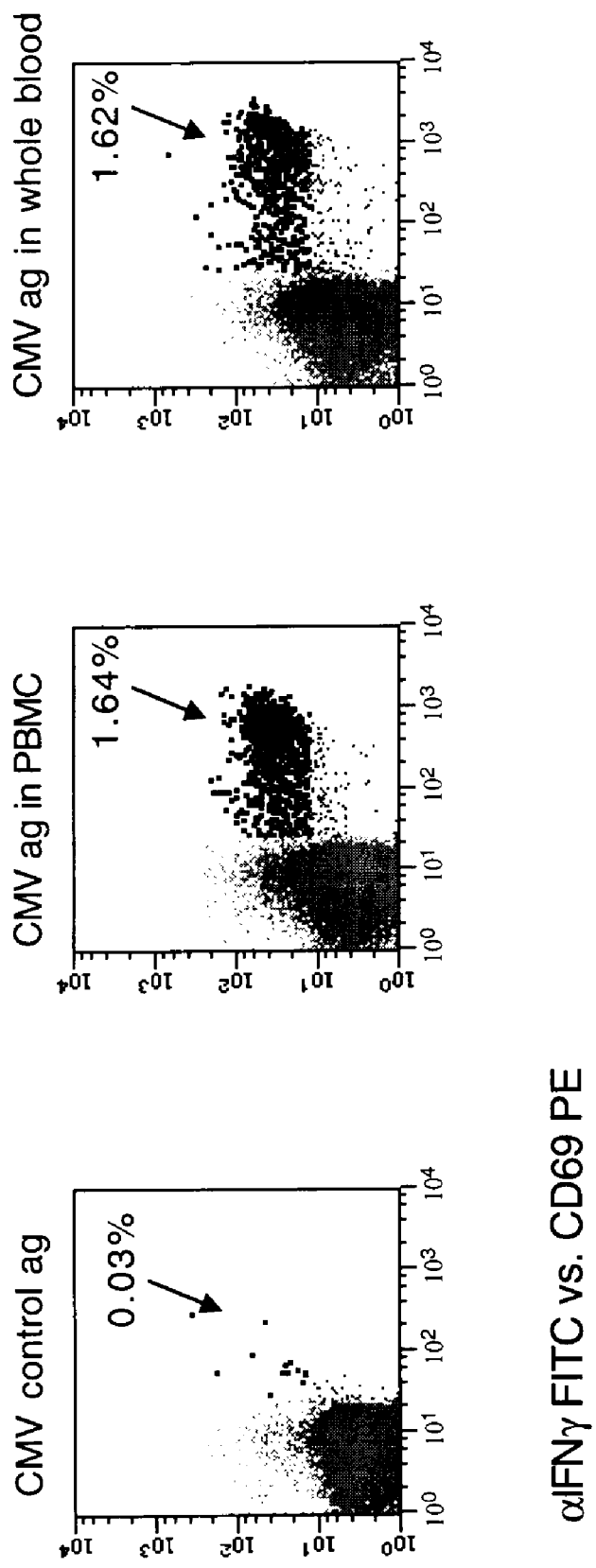

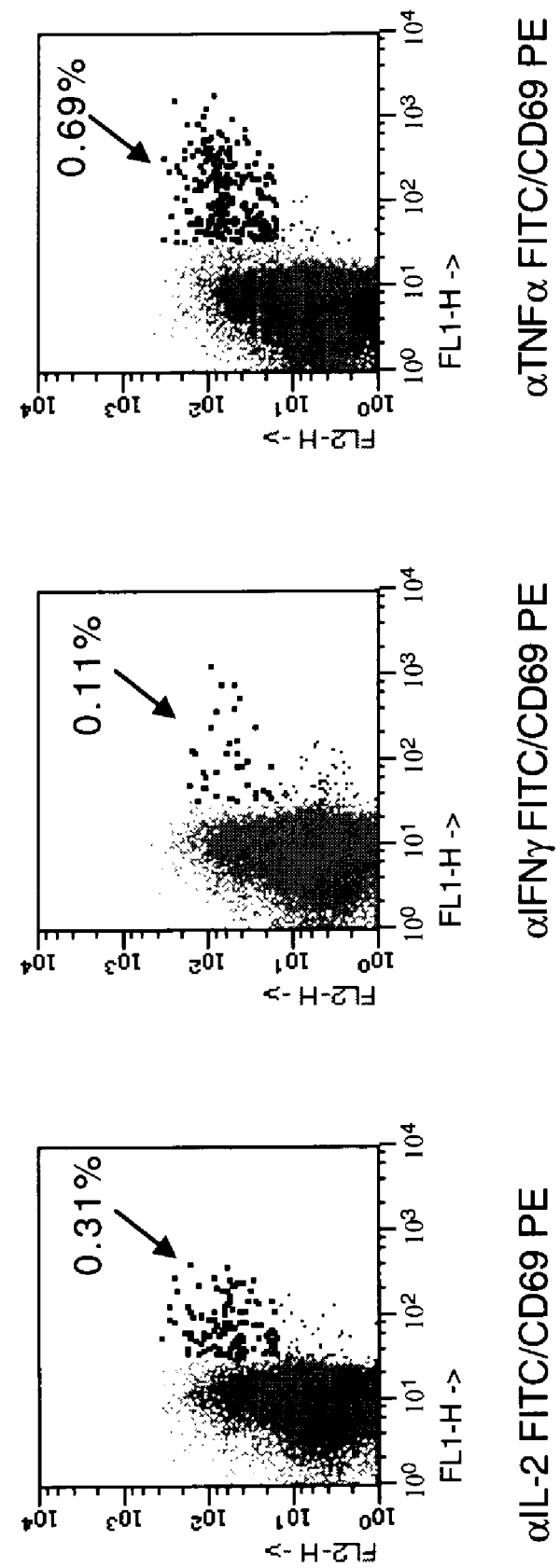

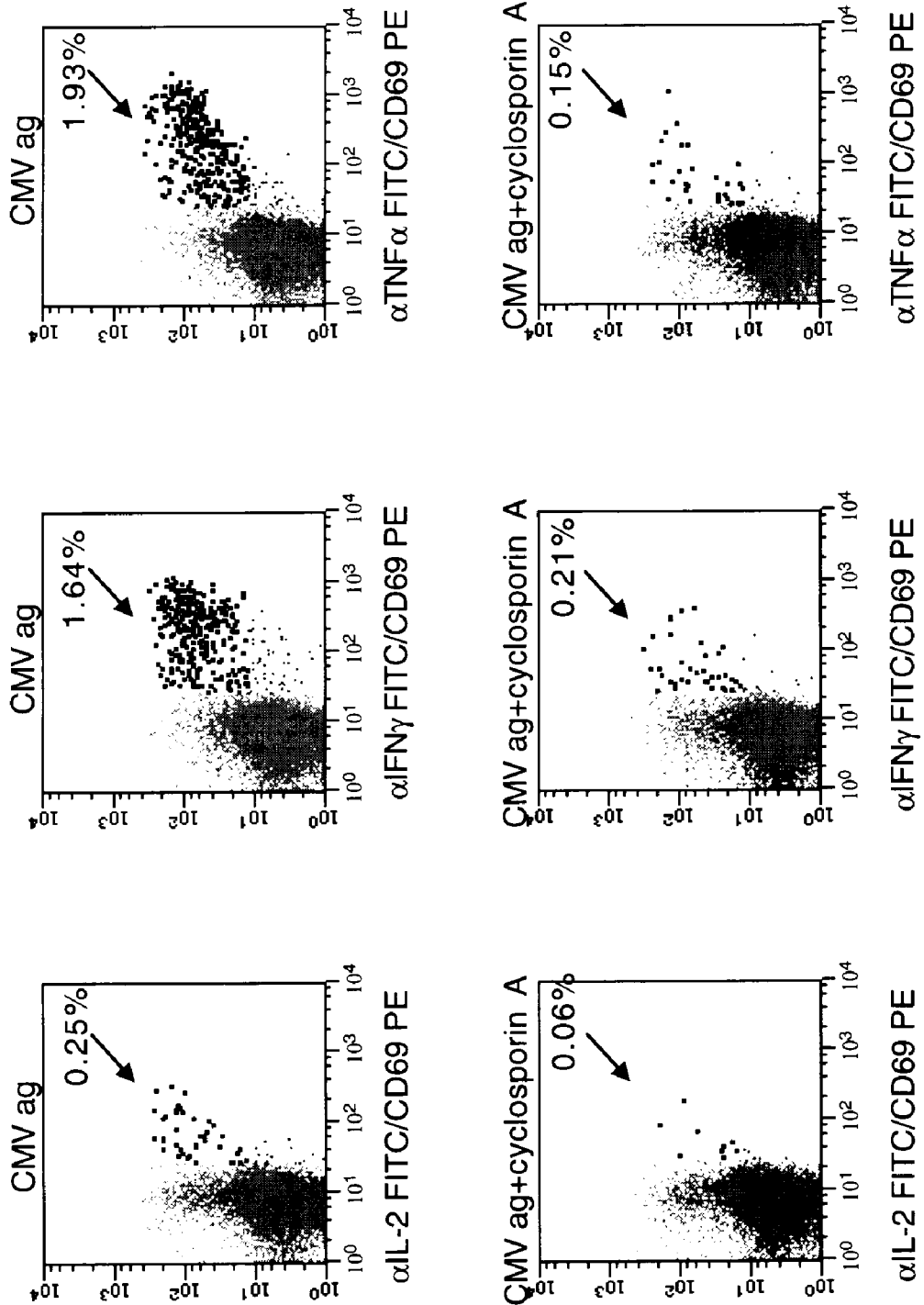

METHOD FOR DETECTING T CELL RESPONSE TO SPECIFIC ANTIGENS IN WHOLE BLOOD

This application is a continuation-in-part of application Ser. No. 08/760,447 filed Dec. 6, 1996 now abandoned.

The invention was made in part with support from the U.S. Government, and the U.S. Government has certain rights in this invention.

BACKGROUND OF INVENTION

Despite widespread agreement that the basic unit of function of the T cell arm of the cellular immune system is the collection of memory/effector T cell clones responsive to a specific antigen (Ag), there is very little understanding of the development and homeostasis of Ag-specific human memory/effector T cells in either health or disease. In large part, this lack of definitive information is methodological; i.e. the simple lack of tools to reliably quantitate and functionally evaluate Ag-specific T cells in the human. For many years, assays of antigen specific T cell function relied on proliferation of cultured PBMC as the measure of the responding T cells.

New knowledge of immunological processes in the past decade, however, have highlighted serious problems with this approach. Proliferative responses require days to manifest, and it is now well documented that many, if not most, memory/effector T cells respond to Ag with an effector response (e.g. cytokine release or cytotoxicity) and then succumb to activation-induced apoptosis prior to any possible proliferative response. Those cells that survive to proliferate are thus a highly variable subset (depending on culture conditions) of the overall Ag-responsive cohort. This issue is even more critical for the evaluation of T function in diseases such as AIDS, as it has been clearly documented that memory/effector T cells from HIV+ individuals display an increased susceptibility to apoptosis, and indeed, show enhanced Ag-induced apoptosis in vitro. Similarly T cell responses to antigen in other diseases may be characterized by varying ratios of cells undergoing proliferation, cytokine expression, apoptosis, or cytotoxic T cell differentiation.

Recently, other assays of T cell function have also included cytokine release endpoints, a defining function of memory/effector T cells. While this addition to the measurement of proliferative responses represents a clear advance, in terms of a more comprehensive measure of T cell activation, these assays do not define the functional cell types that participate in these responses. Further, most of these analyses have relied on ELISA-based quantitation of expressed levels of cytokine in culture supernatants. These procedures yield only bulk measurements; individual cell types participating in the response are not evaluated.

To assess which cell types are expressing selected cytokines, subset purification or single cell-based methodologies such as the ELISPOT and cytokine-release limiting dilution assays have been employed. However, these assays are extremely laborious—especially if set up to measure the multiple, potentially relevant cytokines which may be produced by functionally heterogeneous Ag-specific memory/effector T cells—and therefore are not amenable to routine use in the clinical laboratory. Moreover, the sensitivity of these assays may be limited by (1) conditions which do not mimic in vivo cellular environments which may be more clinically relevant, (2) T cell stimulation conditions that must necessarily compromise between conditions optimal for T cell activation and those compatible with the single cell detection strategy of the assay (e.g. limiting dilution conditions or spot counting on nitrocellulose covered culture wells), and (3) vulnerability to some loss of Ag-reactive cells from activation-induced apoptosis (as these assays require from 1-2 to many days of in vitro culture, and activation-induced apoptosis, as measured by DNA strand breaks, can initiate in as few as 12-19 hours).

It has been previously shown that T cell cytokine responses occur in cells expressing the CD69 antigen. A TH1, or type I response, for example is typically identified as the percentage of CD3+ T cells co-expressing CD69 and γ-IFN, IL-2, or TNF-α. A TH2, type II, response can be characterized as the frequency of CD3+ T cells which co-express CD69, and IL-4 or IL-13. The distribution of individual cytokines of a type I or type II response may also be descriptive of a specific kind of cellular response to antigen. For example unique T cell subsets may express TNF-α and γ-IFN in response to different antigens and have been referred to as TH1 cells.

SUMMARY OF INVENTION

This invention comprises a novel approach to the assessment of Ag-specific T cells that quantitates and characterizes these cells with unprecedented clarity, and importantly, because it is performed in whole blood, is amenable to routine use in the clinical immunology laboratory. In order to evaluate clinical samples for the types of antigen specific cellular responses that reflect in vivo conditions, we have developed an improved flow cytometric intracellular cytokine assay in whole blood that can simultaneously measure multiple T cell subsets expressing multiple cytokines from a single whole blood culture. Evaluation of whole blood antigen specific cytokine responses has the important advantage of assessing T cell activation in the presence of ALL types of MHC autologous antigen presenting cells present in the native sample. It also has the advantage of enabling a culture system (whole blood) which can reflect effects of systemic environments (i.e. drug augmentation or suppression) on T cell responses to specific stimuli including antigen by either culturing in the presence of such drug or analyzing the blood of a human or animal receiving such drug.

At its simplest, the methodology involves a step process, which involves culturing with the antigen specific stimulus and analyzing an aliquot of the cultured sample for expression of one or more intracellular cytokines and/or early activation antigens in combination with one or more T-cell markers, optionally with the lysing of the red blood cells and washing to remove debris.

The method described herein is composed of two parts. The first process relates to the cell culture process for optimal antigen presentation in MHC directed T cell responses (primarily but not restricted to memory CD4+ T cell responses). The second part relates to the analytical (flow cytometry) procedure which enables detection of antigen specific responding T cells based on the expression of an external activation antigen and an intracellular functional cytokine.

More specifically, this invention provides an assay protocol using whole blood for the rapid (generally less than 24 hours, preferably less than 6 hours), highly efficient, Ag-specific activation of secretion-inhibited CD4+ (memory/effector) T cells, followed by the quantization and characterization of these Ag-specific T cells using multiparameter flow cytometric, immunofluorescent detection of one or more intracellular cytokines (including IL-2, IL-4, γ-IFN and TNF-α) and an early activation antigen (such as CD69), in combination with one or more T cell subset-defining phenotypic markers (such as CD3 or CD4). It is further disclosed that the antigen specific response can be more easily detected when the antigen stimulation is provided in conjunction with costimulation of surface antigens involved with accessory cell surface molecules, such as CD28, CD40L , VLA4, and other such specificities known in the art. Costimuli can be either antibodies or ligand binding to these antigens. A preferred costimulus is CD28. It is also determined that T cell responses measured using the protocol defined in this disclosure can be shown to be sensitive to drugs which have been demonstrated to augment or suppress cellular responses (e.g., exogenous cytokines, cyclosporine-A, herbimycin-A).

Further, it has been found intracellular cytokine detection is enhanced when an agent which blocks the secretion of such intracellular cytokines is added during the activation (4 h) period of incubation. A preferred agent is Brefeldin A.

T cells are activated by antigen by autologous antigen presenting cells (APC) (B cells, monocytes, or dendritic cells) which process protein antigen and present resultant peptide determinants on cell surface MHC molecules. We have determined that T cell/APC interactions result in inflammatory reactions that promote enhanced adhesion of APC/T cell aggregates. To detect cognate T-cell responses to specific antigen in suspension for flow cytometric analysis, cation chelators are employed to release reactive T cells into the analysis buffer. EGTA or EDTA are preferred compounds for this purpose.

A preferred methodology of this invention is presented below:

Antigen Activation and Culture of Whole Blood
1. Aliquot 1 ml of heparinized whole blood into tissue culture tubes
2. For enhanced frequency of antigen specific T cell response, add 4μg/ml of CD28 (1μg/10$^6$ cells), incubate 15 min. at RT
3. Add 60μl/ml of antigen (typically 1 to 10μg final per 1 ml culture), incubate for 1 h at 37 C, 7% CO2 (slanted at 5° angle)
4. Add 10μg/ml of BFA, incubate an additional 5 h, with or without agitation
5. Add 100μl of 20 mM Na$_2$EDTA, final concentration 2 mM, vortex, incubate for 15 min. @ RT, wash with PBS with vigorous pippetting.
6. Lyse and fix RBC; e.g. with FACS™ Lysing solution; wash in PBS
7. Proceed to "Staining and detection", or:
8. Freeze in 10% DMSO/1% BSA/PBS at −70C Staining and Detection of Antigen Responsive T cells after Culture in Whole Blood.
1. Thaw cells rapidly in 37 C water bath
2. Wash 2X with cold PBS (at 500×g) for 5 min.
3. Aliquot into FACS tubes, wash with FACS wash buffer
4. Permeabilize cells with 500 μl of FACS™ Permeabilizing Solution for 10 min. at RT
5. Wash with FACS was buffer
6. Stain with MAbs defining intracellular or surface components (e.g. CD3, CD4, cytokines, Brefeldin blocked CD69). Typically CD69 is conjugated to phycoerythrin and anti-cytokine MAbs (IL-2, γ-interferon, and TNF-α) are conjugated with FITC (see examples).
7. Wash and fix with 1% PFA
8. Analyze on FACScan™ (fluorescence trigger on T cell subsets using CD4 PerCP, or CD3 PerCP collect a minimum of 50,000 CD4+ T cell events.

It is to be understood that the above procedures may be modified as conditions dictate, and that a variety of reagents may be used in the permeabilizing and washing steps as would be apparent to the artisan.

For primary cell surface staining of whole blood cultures the procedure is modified as follows. This modification may not be necessary if cell surface epitopes can survive permeabilization procedure. Examples of cell surface-defining reagents that may also be used in intracellular protocols include Leu-4 (CD3), Leu-3a (CD4), and Leu-2a (CD8).

(1) Stain cell surface antigens on T cells using titered concentrations of appropriate monoclonal antibody (e.g. CD45RO) conjugated with fluorochrome; wash and fix with, FACS™ Lysing Solution.

(2) Permeabilize cells exposed to lysing solution with FACS™ permeabilization reagent containing, FACS™ Lysing Soulution+0.025% Tween 20.

(3) Wash in PBS and stain with MAbs detecting intracellular constituents (e.g. CD69+IL-2).

Analysis of responding T cells is based on the percentage of T cells which coincidentally express CD69 antigen and cytokines. We have determined that T cell cytokine responses were predominantly restricted to cells expressing the CD69 antigen. A type 1 (TH1) response, for example is typically identified as the percentage of CD3+ T cells co-expressing CD69 and γ-IFN, IL-2, or TNF-α. A type 2 (TH2) response can be characterized as those CD3+ T cells which co-express CD69, and IL-4 or IL-13, for example. The distribution of individual cytokines of type I or type II responses may also be descriptive of a specific kind of cellular response to antigen. For example unique T cell subsets may express TNF-α and γ-IFN in response to different antigens.

Typically the percentage of memory CD4+ T cells co-expressing CD69 and IL-2 or TNF-α in response to a recall antigen such as mumps or CMV antigen is within the range of 0.15%-3.0% of total CD3+ T lymphocytes. Since this assay procedure measures the frequency of T cell responses to externally processed antigen—most T cell responses will be class II MHC directed and consequently will be CD4+ CD45RO+ T lymphocyte recognitive events. This has been verified by demonstrating that the response to the above mentioned antigens can be blocked by the addition of anti-class II but not anti-class I monoclonal antibodies. Internally processed antigen or class I MHC presented antigen directed responses, however, can be identified by the same set of T cell parameters (i.e. CD69+cytokine expression).

BRIEF DESCRIPTION OF THE FIGURES

FIG. 1: Interferon-γ response in PBMC and whole blood. The illustrated flow dot plot histograms compare the γ-interferon response in antigen specific T cells analyzed either from PBMC purified preparations (middle panel) or from whole blood (far right panel) by multiparameter flow cytometry. The first panel represents CMV control antigen response in T cells analyzed from PBMC preparations. Whole blood analysis of the control antigen response was identical (data not shown). These histograms clearly illustrate that detection sensitivity of cytokine expression in T cells analyzed in PBMC and whole blood is similar.

FIG. 2: Mumps antigen response in whole blood. This figure demonstrates three different T cell cytokine responses to mumps antigen in whole blood. In contrast to FIG. 1 the T cell response to mumps antigen is primarily characterized by expression of TNF-α with a low frequency of cells expressing γ-IFN. These examples highlight the utility of measuring individual cellular cytokine responses which may vary depending on the source of antigen.

FIG. 3: Drug sensitivity of T cell cytokine expression in response to specific antigen. This figure serves to show that this assay can be used to examine drug effects on T cell immunity at the single cell level. The upper row of panels indicates the frequency of CD4+ T cells which express various cytokines (IL-2, γ-IFN, and TNF-α) in response to CMV antigen. The corresponding histograms in the lower panel demonstrate the degree of inhibition of expression by cyclosporine A, a drug used to suppress cellular immune responses in humans. We have also observed both suppressive and enhancing effects of other drugs including hermbimycin, antibodies to accessory molecules and other regulatory cytokines. This figure shows how the described assay can be used to screen drugs which may be targeted to distinct cellular subsets with specific cytokine profiles. This assay may also be used to test the effects of circulating drug in treated patients on specific T cell immunity. The ability to examine cellular responses in whole blood offers the potential to assess drug effects on cellular immunity in a rapid highly informative multiparameter assay.

DETAILED DESCRIPTION OF INVENTION

The instant invention presents a novel method that uses sophisticated, but technically straightforward, flow cytometric method to quantitate and/or phenotypically and/or functionally characterize Ag-specific CD4+ memory/effector human T cells with unparalleled sensitivity in peripheral blood mononuclear cells. Reports in the literature using ELISPOT and limiting dilution type assays suggest precursor frequencies for CMV and mycobacteria reactive T cells in appropriately exposed subjects are on the order of 1/1000 to 1/10,000 mononuclear cell, whereas the flow cytometric assay described here demonstrates precursor frequencies for these Ags in analogous subject populations to be in the 1/1000 to 2/100 CD4+ T cell range. Although some of these differences may be due to variations in subject populations and Ag preparations, these numbers suggest a significant increase in sensitivity between the flow cytometry-based assay and previous assay types, even after correcting for the different denominators of these assays (e.g. total mononuclear cells for limiting dilution and ELISPOT assays; CD4+ T cells for the flow cytometric assay). We have calculated the sensitivity of the flow cytometric assay for intracellular cytokines using calibrated fluorescent beads and 1:1 molar conjugates of PE to antibody to be on the order of 700 molecules per cell. This value contrast with the picogram quantities of cytokine necessary to detect by ELISA.

The increased sensitivity of the flow cytometric assay is likely due to a combination of factors, including 1) the high sensitivity of fluorescence detection by modem flow cytometers, 2) the highly efficient capture of produced cytokine within the cytoplasm of the secretion-inhibited responding cell (as compared to only partial capture in ELISPOT type assays), 3) the independence of culture (stimulation) conditions and signal detection, allowing these culture conditions to be set up with optimization of response as the only concern, and 4) the relatively short stimulation period, which mitigates against the potential negative effect of activation-induced apoptosis on detection efficiency.

The method described in this invention provides a procedure to detect antigen specific T cell responses in whole blood cultures in under 24 h. It has been found that in whole blood cultures, APCs and T cells form adhesive complexes as a consequence of specific antigen activation which prevented detection of responding T cells in cell suspension assays like flow cytometry. The essential modification described herein defines methods for quantitatively recovering small numbers of T cells(<0.1%) from whole blood cultures for analysis from the adhesive antigen-presenting cell (APC) cellular complexes.

Increased sensitivity is not the only advantage of the flow cytometry based assay of this invention. In addition to simplicity, which makes it amenable to routine clinical laboratory testing, this assay also has the significant advantages of being able to assess 1) Ag-specific responses in phenotypically defined T cell subsets, and 2) the synthesis of multiple cytokines in a single Ag-responsive T cell. With respect to the subset delineation, we have used the multiparameter capabilities of this assay to precisely define Ag-specific responses within T cell subsets defined by CD4 vs. CD8, TCR classes, homing receptors, and markers such as CD45RA or CD27. Such subset assignment of the Ag-specific responses allows the separate evaluation of Ag-specific responses in distinct T cell subsets that are potentially independently regulated (e.g. CD4+ vs. CD8+ T cells), and greatly increases the precision and reproducibility of these assays by automatically correcting for potentially confounding changes in the overall representation of a particular T cell subset within the overall PBMC population. Obviously, this capability is particularly germane for the study of CD4+ T cell effector frequencies in HIV+ subjects, whose CD4 counts may vary tremendously.

With regard to the ability to assess multiple cytokines per cell, this assay is the only method described to date that allows the delineation of cytokine secretion patterns of freshly-isolated T cells on an Ag-specific, single cell basis. Although the concept of cytokine synthesis heterogeneity among memory/effector T cell populations (e.g. the TH1 vs. TH2 paradigm) has been well established, it is unclear the extent to which the described cytokine synthesis phenotypes of cloned T cells represent the true spectrum of memory/effector T cell cytokine synthesis function in vitro. Cloned T cells, by definition, spend weeks to months in vitro prior to analysis—during which time functional biases may be introduced by clonal selection and/or inadvertent regulation of effector cell differentiation. The feasibility of determining cytokine synthesis patterns of Ag-specific T cells taken directly from the blood, and stimulated in vitro for only 6 hours. While the predominant pattern of cytokine production of CMV-specific CD4+ T cells from normal subjects is consistent with a classical TH1 phenotype (γ-IFN+/IL-4-), variably-sized subsets of CD4+ T cells synthesizing all or most of the possible combinations of these cytokines on a single cell basis have also been observed.

EXAMPLES

The following examples illustrate certain preferred embodiments of the invention but are not intended to be illustrative of all embodiments.

Example 1

Cell Preparation and Antigen Stimulation

Heparinized whole blood samples were collected from normal or diseased donors using heparin Vacutainer™ blood collection tubes (Becton Dickinson VACUTAINER Systems, Franklin Lakes, N.J.). One ml aliquots of whole blood were dispensed into 16×125 polypropylene tissue culture tubes (Corning Costar Corporation, Cambridge, Mass.).

Appropriately titred specific or control Ag preparations (60 μl/ml) and in most instances (except as noted), 4 μg anti-CD28 MAbs were added to 1 ml whole blood aliquots. Cultures were incubated at a 5° slant at 37° C. in a humidified 5% CO2 atmosphere for 1 hour with slight agitation to improve APC/T cell interaction, and an additional final 5 hours including a final concentration of 10 μg/ml of Brefeldin A (a relatively non-toxic, but potent, inhibitor of intracellular transport which prevents secretion of any produced cytokines. 20 mM Na2EDTA for a final concentration of 2 mM was then added directly to the whole blood cultures. Samples were vortexed and incubated for 15 min. @ RT, washed in PBS with vigorous pipptetting. Whole blood samples were subsequently RBC lysed and fixed with FACSlysing™ solution (Becton Dickinson) and washed in PBS. plus 1% BSA prior to resuspension @ 5×10⁶ cells/ml in freezing medium (10% dimethyl sulfoxide in dPBS with 1% BSA). Finally, the cells were frozen in 2 ml Wheaton vials at −70° C. in a Nalgene (Rochester, N.Y.) freezing chamber.

Example 2

Immunofluorescent Staining

Cell preparations frozen as described above were rapidly thawed in a 37° C. water bath and then washed once with cold dPBS prior to resuspension in fixation/permeabilization solution (Becton Dickinson Immunocytometry Systems, San Jose, Calif.) at 1×10⁶ cells/500 ul, and incubation for 10 minutes at room temperature in the dark. These cells were washed twice with dPBS with BSA and sodium azide, and then were stained protected from light with directly conjugated MAbs for 30 minutes. In some experiments, the freezing step was omitted, and cells freshly harvested after Ag activation were cell surface stained first, and then fixed/permeabilized/washed, and then stained for intracytoplasmic Ags. After staining, the cells were washed, refixed in 1% paraformaldehyde in dPBS, and then kept protected from light at 4° C. until analysis on the flow cytometer.

Example 3

Flow Cytometric Analysis

Up to six parameter analysis was performed on a modified FACSort™ (Becton Dickinson) flow cytometer equipped with a second 532 nm line diode laser (BDIS) using FITC, phycoerythrin(PE), and peridinin chlorophyll protein (PerCP), and allophycocyanin (APC) as the 4 fluorescent parameters, using methods of cytometer set up and data acquisition which are well known in the art. Otherwise 5 parameter analysis using up to three fluorescent parameters was conducted on a standard FACScan™ flow cytometer. For a typical analysis, 50,000 events were acquired, gated on CD4 expression and a light scatter gate designed to include only viable lymphocytes (most files required "fine-tuning" of gating during analysis on these same parameters, leaving 48,000 events for the final profiles). In some analyses, additional "live" gating based on a fluorescent parameter (for example, CD69 reactivity) was performed to enhance the sampling of small populations. List mode multiparameter data files (each file with forward scatter, orthogonal scatter, and 3-4 fluorescent parameters) were analyzed using the PAINT~A~GATE$^{Plus}$™ program (BDIS). Isotype-matched negative control reagents were used to verify the staining specificity of experimental antibodies, and as a guide for setting markers to delineate "positive" and "negative" populations.

Example 4

Establishment of a Flow Cytometric Assay of Ag-Specific T Cell Cytokine Responses Previous methods for detecting and quantitating T cell cytokine responses to polyclonal mitogens (e.g. phorbol ester plus ionomycin) and superAgs (the staphylococcal enterotoxin superAgs SEA and SEB) using a protocol based on intracytoplasmic staining of cytokine in short-term activated, secretion-inhibited T cells and multiparameter flow cytometric analysis has been previously known. It was initially anticipated that, with slight modifications, this approach would identify and quantitate T cells producing cytokine in response to nominal Ags as well. However, Ag responses differed from mitogen and superAg responses in several key areas. First, the geometry of the T cell/accessory cell interaction was critical for Ag responses; maximal responses were observed in slant tubes that allowed close proximity of T cells and accessory cells, but still allowed adequate media access to responding cells. Second, responses were maximized when Brefeldin A was omitted from the initial hour of interaction (likely to allow optimal antigen processing), and when exogenous costimulation was provided. Third, precise detection of responding T cells was enhanced with inclusion of CD69 assessment in the multiparameter protocol. CD69 is upregulated on activated T cells prior to cytokine production, and thus allows more definitive "clustering" of the true responding fraction. Background staining, when present, is often only present in the CD69 negative fraction, and thus can be excluded from consideration. CD69 can also be used as a live gating parameter to enhance collection of the cytokine producing cells, yet still allow back calculation of responding cell frequency to overall CD4+ population. Finally, because of the relatively small size of the Ag-specific populations, accurate assessment of these responses required the routine collection and analysis of at least 50,000 events per determination.

In order to allow antigen specific reactions to occur in whole blood environments additional modifications were required. Key elements in these modifications were: (1) Slight agitation during the first hour of incubation of whole blood cultures with antigen to improve APC interactions with specific T cells, (2) use of polypropylene culture tubes to more easily displace T cells from adherent APC complexes, (3) direct addition of EDTA to whole blood cultures to optimize recovery of antigen-activated T cells. FIG. 1 compares frequencies of CD4+ T cells responding to CMV antigen. This figure illustrates similar T cell response behavior in both PBMC and whole blood environments (e.g. when samples are obtained from normal donors). FIG. 2 demonstrates that T cell responses to other cognate antigens such as mumps virus can also be measured using whole blood culture methodology. In contrast to the CMV response example 1, T cell responses to mumps in this individual exhibits a proportionally higher frequency of T cells expressing TNF-α and a smaller frequency of CD4+ T cells expressing γ-IFN.

Example 5

Assessment of Drug Effects on Antigen Specific Reactions in Whole Blood

Concentrations (typically less than 1 μg of immunosuppressive drug (e.g. Cyclosporine A, Herbimycin A) were added to initial whole blood cultures activated by antigens as described in example 1. Frequencies of CD4+ T cells responding to various antigen in the presence or absence of drug were compared as determined by flow cytometry as detailed in example 2 and example 3. FIG. 3 (example 3) shows the suppressive effects of the addition of 1 μg of cyclosporine A to antigen specific T cell responses in whole blood cultures. In this example, 75% inhibition of IL-2, 87% of γ-IFN and 92% of TNF-α T cell responses to CMV were blocked by cyclosporine A. This example shows how the whole blood assay can be used to assess immunosuppressive or augmenting effects of immunomodulatory drugs. A corollary to this assay is that effects of in vivo concentrations of drugs may be also be assessed. Since the assay is performed in the presence of autologous plasma, T cell responses can be measured in the presence of pharmacological concentrations of administered drugs.

It is apparent that many modifications and variations of this invention as hereinabove set forth may be made without departing from the scope and the spirit thereof. The specific embodiments are given by way of example only, and the invention is limited only by the terms of the appended claims.

What is claimed is:

1. A method of detecting T lymphocytes that are specific for a nominal antigen, comprising:
   culturing a sample containing peripheral blood mononuclear cells with a nominal antigen;
   adding to said sample an inhibitor of cytokine secretion;
   permeabilizing said cells;
   adding to said sample at least one cytokine-specific antibody and at least one T lymphocyte subset-defining antibody; and then
   flow cytometrically detecting the intracellular binding of said cytokine-specific antibody by cells in the defined T lymphocyte subset.

2. The method of claim 1, further comprising the step of adding to said sample, contemporaneously with antigen contact, a costimulus of T cell activation.

3. The method of claim 2, wherein said costimulus is an antibody specific for CD28.

4. The method of claim 2, wherein said costimulus is an antibody specific for VLA-4.

5. The method of claim 1, further comprising contacting said sample with an antibody specific for a T lymphocyte early activation antigen, and then flow cytometrically detecting the intracellular binding of said cytokine-specific antibody by cells in the defined T lymphocyte subset that concurrently bind said early activation antigen-specific antibody.

6. The method of claim 5, wherein said T lymphocyte early activation antigen is CD69.

7. The method of any one of claims 1, 2, or 5 wherein said sample is a whole blood sample.

8. The method of claim 7, further comprising the step of adding a cationic chelator after antigen contact is complete but prior to flow cytometric detection.

9. The method of claim 8, wherein said chelator is EDTA or EGTA.

10. The method of claim 9, wherein said chelator is EDTA.

11. The method of claim 7, further comprising the step of lysing red blood cells.

12. The method of claim 1, wherein said nominal antigen is selected from the group consisting of alloantigens, autoantigens, viral antigens, and bacterial antigens.

13. The method of claim 12, wherein said nominal antigen is a viral antigen.

14. The method of claim 13, wherein said antigen is a CMV antigen.

15. The method of claim 13, wherein said antigen is a mumps antigen.

16. The method of claim 13, wherein said antigen is a measles antigen.

17. The method of claim 12, wherein said MHC-dependent nominal antigen is a bacterial antigen.

18. The method of claim 17, wherein said antigen is a Mycobacterium tuberculosis antigen.

19. The method of claim 1, wherein said inhibitor of cytokine secretion is Brefeldin A.

20. The method of claim 1, wherein said cytokine-specific antibody is specific for a cytokine selected from the group consisting of: IL-2, IL-4, IL-13, γ-IFN, and TNF-α.

21. The method of claim 20, wherein said cytokine-specific antibody is specific for IL-2.

22. The method of claim 20, wherein said cytokine-specific antibody is specific for IL-4.

23. The method of claim 20, wherein said cytokine-specific antibody is specific for γ-IFN.

24. The method of claim 20, wherein said cytokine-specific antibody is specific for TNF-α.

25. The method of claim 1, wherein said T lymphocyte subset-defining antibody is selected from the group consisting of antibodies specific for: CD3, CD4, CD8, TCR, homing receptors, CD45RO, CD45RA and CD27.

26. The method of claim 25, wherein said T lymphocyte subset-defining antibody is specific for CD3.

27. The method of claim 25, wherein said T lymphocyte subset-defining antibody is specific for CD4.

28. The method of claim 25, wherein said T lymphocyte subset-defining antibody is specific for CD8.

29. The method of any one of claims 1, 2, or 5 wherein said anti-cytokine antibodies, said T lymphocyte subset-defining antibodies, and said early activation antigen-specific antibodies are each conjugated directly to fluorophores.

30. The method of claim 29, wherein said fluorophores are selected from the group consisting of FITC, PE, PerCP, and APC.

31. The method of claim 30, wherein said anti-cytokine antibodies are conjugated to FITC.

32. The method of claim 30, wherein said T lymphocyte subset-defining antibodies are conjugated to PerCP.

33. The method of claim 30, wherein said antibody specific for a T lymphocyte early activation antigen is conjugated to PE.

34. The method of any one of claims 1, 2, or 5 wherein said antigen-contacting step lasts no longer than 24 hours.

35. The method of claim 34, wherein said antigen-contacting step lasts no longer than 6 hours.

36. The method of claim 1, wherein each of said at least one cytokine-specific antibody is specific for a cytokine selected from the group consisting of IL-2, IL-4, IL-13, IFN-γ, and TNF-α.

37. The method of claim 36, further comprising the step of adding to said sample, contemporaneously with antigen contact, a costimulus of T cell activation, wherein said costimulus is selected from the group consisting of antibodies specific for CD28, VLA-4, CD86, or CD118.

38. The method of claim 36, further comprising contacting said sample with an antibody specific for CD69, and then flow cytometrically detecting the intracellular binding of said cytokine-specific antibody by CD69+ cells in the defined T lymphocyte subset.

39. A method of detecting T lymphocytes that are specific for a nominal antigen, comprising:
   culturing a sample containing peripheral blood mononuclear cells with a nominal antigen in the presence of Brefeldin-A;
   permeabilizing said cells;
   adding to said sample at least one cytokine-specific antibody and at least one T lymphocyte subset-defining antibody; and
   flow cytometrically detecting the intracellular binding of said cytokine-specific antibody by cells in the defined T lymphocyte subset.

40. A method of detecting T lymphocytes that are specific for a nominal antigen, comprising:
   culturing a sample containing peripheral blood mononuclear cells with a nominal antigen in the presence of Brefeldin-A, wherein said culturing is carried out in a slant tube;
   permeabilizing said cells;
   adding to said sample at least one cytokine-specific antibody and at least one T lymphocyte subset-defining antibody; and flow cytometrically detecting the intracellular binding of said cytokine-specific antibody by cells in the defined T lymphocyte subset.

41. A method of detecting T lymphocytes that are specific for a nominal antigen, comprising:

culturing a sample containing peripheral blood mononuclear cells with a nominal antigen in the presence of Brefeldin-A, wherein said culturing is carried out in a slant tube;

permeabilizing said cells;

adding to said sample at least one cytokine-specific antibody and at least one T lymphocyte subset-defining antibody; and flow cytometrically detecting the intracellular binding of said cytokine-specific antibody by cells in the defined T lymphocyte subset, wherein said step of flow cytometrically detecting the intracellular binding of said cytokine-specific antibody by cells in the defined T lymphocyte subset comprises analyzing at least 50,000 cells.

* * * * *